United States Patent [19]
Kagan et al.

[11] Patent Number: 5,755,698
[45] Date of Patent: May 26, 1998

[54] THORACIC CATHETER PROTECTOR HARNESS

[76] Inventors: Karen L. Kagan; Neil A. Kagan, both of 7562 Volga La.#2, Huntington Beach, Calif. 92647

[21] Appl. No.: 778,613
[22] Filed: Jan. 6, 1997
[51] Int. Cl.⁶ ................................ A61M 25/02
[52] U.S. Cl. .................. 604/179; 604/174; 604/180; 128/DIG. 26
[58] Field of Search ................... 604/174, 178, 604/179, 180; 128/DIG. 26

[56] References Cited

U.S. PATENT DOCUMENTS

| | | |
|---|---|---|
| 3,765,421 | 10/1973 | Poprik . |
| 3,878,849 | 4/1975 | Muller et al. . |
| 4,087,864 | 5/1978 | LaBove et al. ............ 604/174 X |
| 4,416,664 | 11/1983 | Womack . |
| 4,574,798 | 3/1986 | Heitzman ............. 128/DIG. 26 X |
| 4,578,062 | 3/1986 | Schneider ............. 128/DIG. 26 X |
| 4,582,508 | 4/1986 | Pavelka .................... 604/179 |
| 4,666,432 | 5/1987 | McNeish et al. ............ 604/179 X |
| 4,671,787 | 6/1987 | Widman . |
| 4,799,923 | 1/1989 | Campbell . |
| 5,037,397 | 8/1991 | Kalt et al. . |
| 5,048,512 | 9/1991 | Turner et al. ............ 604/179 X |
| 5,336,195 | 8/1994 | Daneshvar ............... 604/179 |
| 5,352,209 | 10/1994 | Bird et al. . |
| 5,403,285 | 4/1995 | Roberts ................... 604/179 |
| 5,417,668 | 5/1995 | Setzer et al. . |
| 5,496,282 | 3/1996 | Militzer et al. . |

*Primary Examiner*—Sam Rimell
*Attorney, Agent, or Firm*—Fulwider Patton Lee & Utecht LLP

[57] ABSTRACT

The invention is a catheter protector harness apparatus. The protective apparatus as worn by an adult, child or infant has a belt that encircles the body from the chest to the back by passing under the arms and which has at least one strap passing over a shoulder. The harness belt and strap are secured behind the back out of reach, if desired, and the catheter is enclosed in a pocket mounted upon the front of the harness belt and formed by folding a flap which depends from the front portion of the harness belt and which is folded about an imaginary hinge-line extending along the front middle portion of the belt to which the flap is attached and which rests against the chest of the patient's body.

15 Claims, 3 Drawing Sheets

THORACIC CATHETER PROTECTOR HARNESS

BACKGROUND OF THE INVENTION

1. Field of the Invention

The present invention relates to a Thoracic Catheter Protector Harness, and more particularly to a catheter protector harness apparatus which will prevent injury to the catheter entry site into the patient's body.

2. Description of the Prior Art

Efforts have been made in the past to eliminate the need to employ medical tape to secure the external portion of implanted catheters to the skin of a patient. The tape can be inadvertently or intentionally removed by the patient prematurely thereby leaving the catheter unsecured and exposed from the insertion site in the skin where it enters the body. The unsecured catheter is then susceptible to being accidentally displaced or even pulled completely out of the body causing severe discomfort, tissue damage, and possible infection which requires implementation of infection control measures and may necessitate additional surgery to repair tissue damage and replace the catheter. Additionally, it is well-known that the necessarily repeated cleaning and disinfection of the catheter entry site into the body requires frequent removal and reapplication of medical tape on the sensitive skin of patients, especially infants and young children, which causes itching, severe irritation and soreness. Attempts to eliminate the need for taping have led to the development of covers for enclosing and protecting the external portion of the catheter and which are affixed to the patient's skin with a less irritating medical grade adhesive similar to but less irritating than that employed by regular medical tape. Devices of this sort are undesirable to the catheter patient because the use of any adhesive, over time, results in the same type of skin irritation and soreness associated with the use of regular medical tape. Furthermore, the adhesive used with these devices typically employs lower adhesion capability causing more frequent, premature departure from the skin. U.S. Pat. No. 5,417,668 to Setzer et al. appears to disclose such an apparatus.

Other efforts have led to the development of protective covers which enclose the external portion of the implanted catheter inside an integrally formed pocket, which covers are affixed to the body of the patient by employing an elastic belt of fabric designed to encircle the patient's body. Such devices typically incorporate an opening through the belt fabric positioned near the implant site so that the external segment of the catheter tubing may pass through the opening from the interior of the belt to the exterior. Once threaded through the opening, the catheter is then enclosed within a protective cover integrally formed on the exterior of the belt. It is proposed that the catheter be held in place within the protective cover with hook and pile type fastening tabs on the exterior of the belt which tabs are also within the protective cover. The protective cover is often formed as a flap formed integral to the cover and folded over a portion of the cover to form a pocket and held in place over the catheter by the use of hook and pile fastening means. A device of this type is disclosed by U.S. Pat. No. 5,403,285 to Roberts. Protection devices of this type suffer the shortcoming that the belt may be easily rotated about the patient's torso thus tending to dislocate the catheter causing injury to the implant site. As the belt is rotated, it unavoidably imparts a shearing action to the catheter at the skin entry site which, when of sufficient magnitude, will cause the skin to tear thereby inflicting said injury and creating the need for treatment to control possible infection and surgical repair of the tear in the skin and replacement of the catheter in the event the catheter is disturbed from the implanted location.

Further efforts to secure and protect the external portion of catheters have resulted in the creation of devices having various types of protective covers attached to many types of belts or straps. However, each of these devices either uses adhesive, incorporates an opening through which the catheter must pass or is configured to be easily removed making it undesirable for use with an infant or young child. In particular, these devices appear to have been directed specifically for use with urinary or dialysis catheters being adapted to restrain the catheter about the leg, arm or waist of the patient. As an illustrative example, the devices shown in U.S. Pat. Nos. 3,765,421, 3,878,849, 4,416,664, 4,671,787, 5,037,397, and 5,352,209 are seemingly restricted to securing various types of catheters either to the skin surface, a limb or about the waist, and failing in every case to adequately protect the external end of the catheter from accidental damage. The device detailed in U.S. Pat. No. 4,799,923 discloses an example of a device which provides an enclosure for protecting an external end of a catheter and which incorporates an opening through the belt. A catheter passing through such an opening would be subjected to the shearing action problems previously described rendering it undesirable for use with patients. The dialysis catheter protection apparatus described in U.S. Pat. No. 5,496,282 to Militzer et al. also appears to provide an enclosure for protection and securing of the catheter, but it too falls far short of adequately protecting the entry site of the catheter into the body. Also, this apparatus is easily removed by the wearer and, further, fails to disclose any means to adequately prevent rotation of the belt about the torso thus making the belt undesirable for use with adults, infants or young children.

Adults, infants and young children whose medical condition necessitates the imnplantation of a catheter in their torso have long been exposed to the danger of serious injury from the accidental dislocation or premature removal of the catheter for the above stated reasons. None of the previous devices have adequately protected both the external segment of the catheter and the entry site into the body from these problems giving rise to increased risks of serious injury among adults and especially infants and young children having implanted catheters. Thus, it is apparent that a need exists for an apparatus which not only protects the external end of a catheter and secures it to the body, but which provides a means for protecting the entry site from the described sources of injury.

SUMMARY OF THE INVENTION

The catheter protector harness of the present invention is intended to hold and protect the external segment of an implanted catheter used to administer and withdraw fluids from an adult, child or an infant. Catheters of this type incorporate at least a single lumen extending within the body and positioned within either a venous and or an arterial blood vessel. The external portion of the catheter has at least a single injection or withdrawal port comprised by any of a number of different types of medical tubing in combination with connector devices comprising resealable injection and withdrawal ports or Luer lock fittings to name a few. The catheter protector harness invention protects the external segment of the catheter by enclosing it within an integrally formed pocket of fabric or other material, snugly securing it to the outside of the body from which the implanted catheter extends. The protective apparatus worn by the patient has an elongated fabric belt which is adapted to encircle the body from the chest around to the back by passing each opposite end under the arms of the patient and to connect together behind the back with releasable hook and pile fastener means disposed at the opposite ends of the belt. The harness belt has straps attached at one end to the middle front portion of the harness belt proximal to the chest and which each pass over a shoulder being attached at their respective opposite ends to the back ends of the harness belt thereby preventing the harness from rotating about the body by engaging the shoulders of the body. The harness belt and straps are secured behind the back out of reach of the wearer to ensure that the harness may be removed only with assistance thus preventing the wearer from inadvertently or accidentally removing the harness and later inflicting damage to the implanted catheter, if such prevention is desirable. The harness belt is wide enough about its thinner cross section so that the site where the catheter exits the body is fully covered over by the harness belt portion for purposes of protection of the catheter entry site from unwanted disruption or accidental displacement. The catheter is protectively enclosed in a pocket integrally mounted upon the front-most, medial portion of the harness belt. An elongated, rectangular flap is integrally formed with the harness belt being attached at one of four sides and depending downwardly from the front portion of the harness belt. The pocket is formed by folding the flap about an imaginary hinge-line along the side attached to the medial portion of the harness belt, up and underneath, or outside, the harness belt so that the external end of the catheter is sandwiched between the harness belt and the flap with the flap resting underneath or outside the harness belt against the chest. In this particular embodiment, the other three non-connected sides of the flap have hook type fastening means located along each peripheral edge such that when the flap is folded up and underneath the harness belt, the hook fastening means releasably engage cooperatively positioned pile fastening means fixedly disposed on the underside, or the outside, of the harness belt. As the hook and pile fastening means at the peripheral edges of the formed pocket engage one another, the catheter tubing is loosely secured thereby such that normal body movement will not injuriously disturb the catheter entry site into the body while the catheter is protectively secured within the harness pocket. The harness apparatus itself will not shift appreciably about the torso because the shoulder straps affirmatively engage the shoulders in the event any rotational displacement of the harness is experienced thereby preventing any harmful rotation of the harness belt.

The fastening devices are purposefully designed to be located out of the reach and behind the wearer's back and underneath the front of the harness belt against the chest to virtually guarantee that the wearer is prevented from accidentally or intentionally displacing either the harness itself, the catheter tubing located at the entry point into the body or the protectively enclosed external segment disposed with the pocket. Furthermore, the exit site of the catheter from the body is covered over by the harness belt thus being protected from inadvertent disruption and removal further reducing the risk of resultant injury. Therefore, an adult, infant or young child patient having an implanted catheter and outfitted with this novel catheter protector harness apparatus completely avoids exposure to the foregoing, and heretofore unavoidable, dangers.

BRIEF DESCRIPTION OF THE DRAWINGS

Referring now to the drawings wherein like reference numerals across the several different views refer to identical or corresponding parts.

DETAILED DESCRIPTION OF A PREFERRED EMBODIMENT

Figure 1:
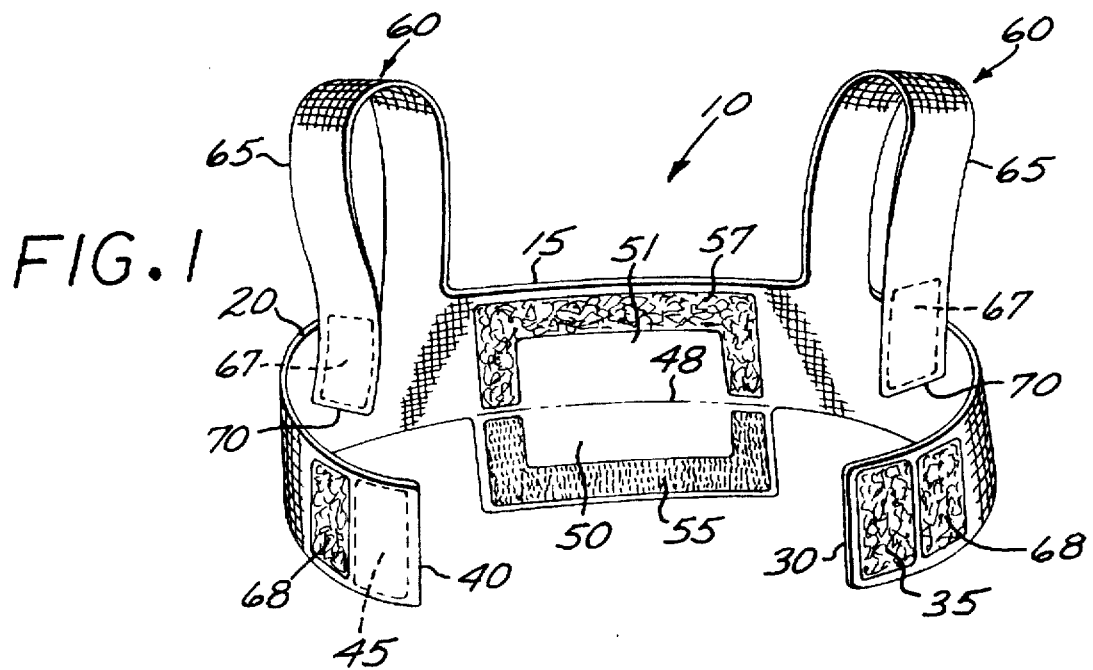
FIG. 1 is a perspective view of a Thoracic Catheter Protector Harness embodying the present invention.

As shown in the drawings for purposes of illustration, the present invention comprises a thoracic catheter protector harness apparatus which obviates many of the problems associated with catheters implanted in adults, infants and small children. The problems encountered are easily solved by the invention disclosed herein which can be inexpensively manufactured, either in mass quantity or on a custom order basis, from a variety of readily available materials and which is easily affixed to an infant, young child or adult.

One object of this invention is to adequately protect a catheter implanted in an adult, infant or young child from accidental, injurious displacement or premature withdrawal without the use of tape and which, by design, both prevents rotation of the harness and protects the catheter entry site from either harness induced shearing forces or other external disturbances.

Another object of the invention is to place the fastening devices for attaching the harness belt and for protecting the catheter out of reach of the infant, young child or incapacitated adult so that the catheter protector harness apparatus can be easily removed only with assistance.

Additional novel features, advantages over previous devices and objects of the inventor will become readily apparent from the embodiments described by the following detailed description of the invention when considered in conjunction with the accompanying drawings.

Figure 2:
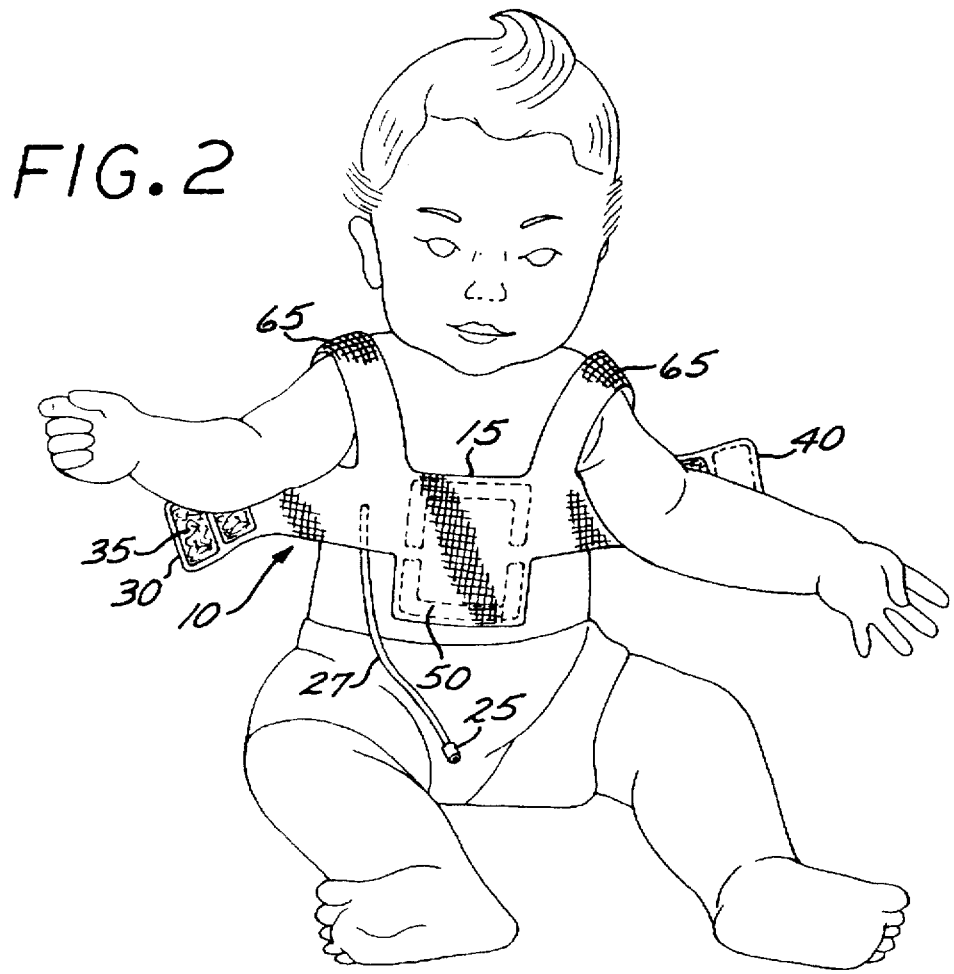
FIG. 2 is a perspective view, in reduced scale, showing the catheter protector harness apparatus of FIG. 1 being placed on an infant or small child.
Figure 3:
FIG. 3 is a front planar view, in reduced scale, of the Thoracic Catheter Protector Harness in FIG. 1 placed on an infant or small child.
Figure 4:
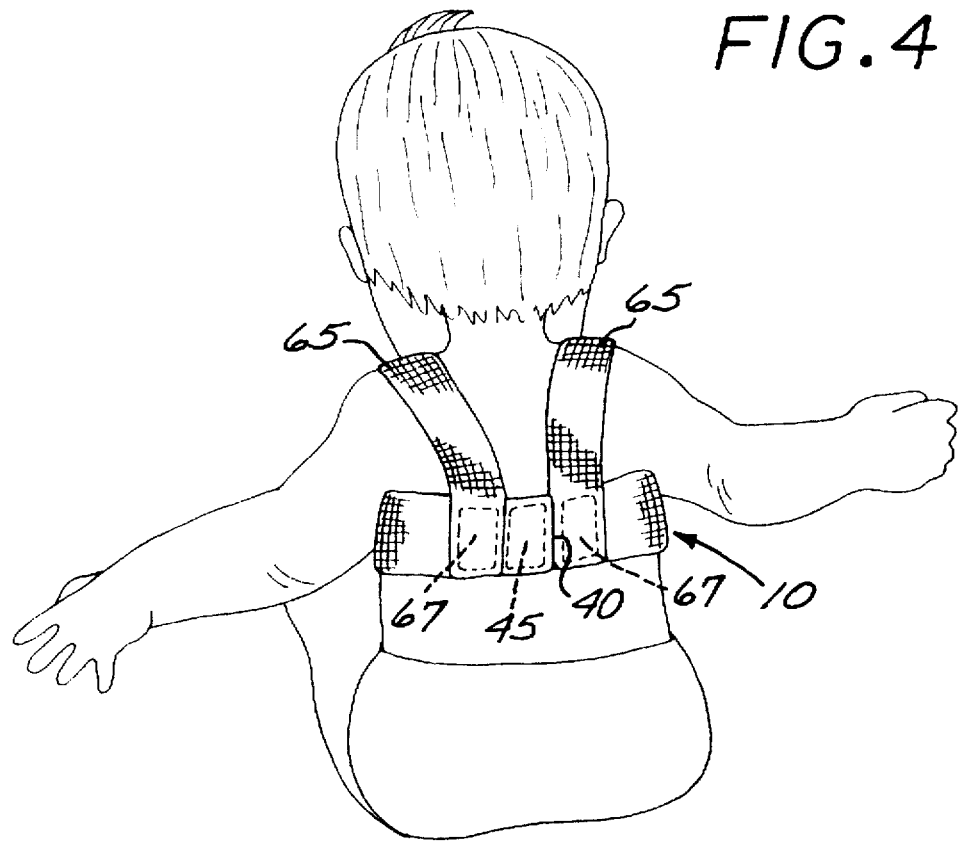
FIG. 4 is a rear planar view, in reduced scale, of the Thoracic Catheter Protector Harness in FIG. 1 placed on an infant or small child.
Figure 6:
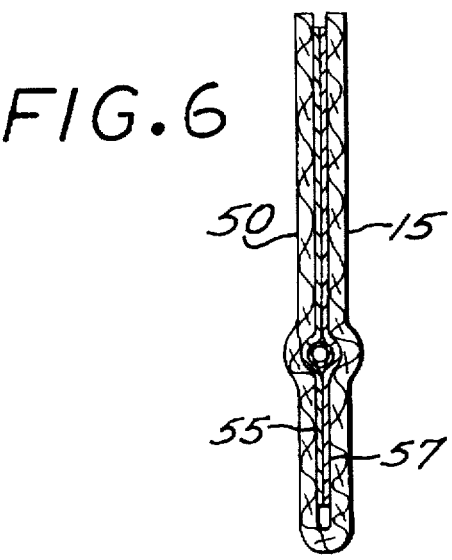
FIG. 6 is a cross-sectional view, in enlarged scale, taken along section line 6—6 of FIG. 3 with the catheter secured.

Referring now to the drawings, the thoracic catheter protector harness apparatus according to the present invention is illustrated in FIG. 1 and shown generally at reference numeral 10. As depicted in FIG. 2, harness 10 is attached to the patient's body with a fabric belt 20 encircled about the torso with the opposite ends 30 and 40 fastened to one another with hook and pile fasteners 35 and 45. Rotation of fabric belt 20 is prevented by stabilizing device, shown generally at reference numeral 60, formed by straps 65 which rise up from the front middle section 15 of belt 20 over the shoulders of the patient and attach by hook and pile fasteners 67 proximal to the opposite ends 30 and 40 of belt 20 (FIG. 1 and 4). Once affixed to the patient, the external segment of catheter tubing 27 and end connector 25 are positioned underneath, or outside, front middle section 15 of belt 20 and against the chest of the patient (FIG. 3). Next, integral flap 50 is folded up and underneath, or outside, harness belt 20 about imaginary hinge-line 48 thereby sandwiching catheter tubing 27 and end connector 25 between flap 50 and front middle section 15 (FIG. 3). As integral flap 50 is folded up and underneath front middle section 15, hook fastener 55 is, by design, properly positioned to cooperatively engage corresponding pile fastener 57 such that the pocket formed between flap 50 and front middle section 15 is secured on the three sides bordered about the peripheral edges by fasteners 55 and 57. It can be understood from observing this configuration that the catheter tubing 27 passes across the pocket boundary established by hook and pile fasteners 55 and 57 and is thus slidably and snugly secured within the formed pocket (FIG. 3 and 6).

The catheter protector harness 10 described above can be mass produced or custom manufactured without difficulty from a variety of readily available and inexpensive materials. Typically, a woven fabric is used which is adapted for repeated washing and drying in household appliances making for effortless clean-up and suitability for use with all types of catheter implant patients. A reasonably comfortable, elastic or elasticized primarily cotton material, or equally desirable alternative, of the desired solid color or with a desired pattern of color(s) and or design(s) is preferred which is naturally non-irritating to the skin of most adults, children and infants. The best mode of this invention employs an elastic or elasticized, primarily cotton material to ensure a snug fit although such is not required in light of the many inexpensive and desirable alternatives. The hook and pile fastening means employed for the harness belt 20 and the straps 65 allow for an adjustable configuration which would permit a comfortable snug fit without the use of an elastic material. The primarily cotton or other equally desirable alternative material may be pre-treated with suitable chemicals and or treatments which are known to prevent or resist staining, absorption or degradation upon exposure to blood, medical or other bodily fluids and substances. Other reusable and disposable materials are readily available (e.g. those presently used for hospital gowns, surgical smocks and masks) which are well suited for construction of this invention. In fact, health care facilities concerned with infection control and minimization of waste materials may in some short-term care or high-infection-risk situations prefer more inexpensive, disposable materials which are easily disinfected, incinerated or otherwise disposed of within the capabilities of existing nosocomial systems. While an elastic or elasticized, absorbent, soft and breathable primarily cotton material is often preferred for those portions of the harness in contact with the patient's skin, the pocket portion 51 and the flap 50 which cooperate to form a protective compartment for the catheter 27 and end 25, may be constructed entirely or in combination with a plastic, plasticized or other material treated by methods known to the art which result in the pocket compartment material being incapable of or resistant to staining, absorption, or deterioration caused by exposure to blood, medical or other bodily substances and designed for quick and easy cleaning such that the entire harness need not be cleaned every time medical fluids or blood contact the material within the compartment formed by pocket portion 51 and flap 50. In this configuration, the end 25 may be protectively stored within the protective compartment while wrapped lightly in absorptive cotton or medical gauze which is easily and inexpensively replaced.

The fastening means employed for this particular preferred embodiment comprises the inexpensive Velcro® material which is well-suited to repeated use and clean-up and which is available from a wide array of well-known vendors in many colors, shapes and sizes. Although the preferred embodiment discloses linearly shaped fastening strips disposed about the peripheral edges of the flap 50 and pocket boundaries formed by fastening means 55 and 57, any number of possible combinations, shapes and sizes may be employed with equal success. Moreover, hook and pile fasteners are only one among a number of suitable and widely-available fastening means which also include medical grade adhesives which can be used repeatedly and may in some instances be successfully washed and cleaned without a resulting deterioration of adhesive capability of the fastener.

The wide range of suitable configurations of this invention may be easily extended beyond the disclosed harness configuration of the preferred embodiment to include adaptability to regular clothing items such that patients fitted with catheter implants may engage in activity or rest as if having no implanted catheter without the heretofore associated risks of injury to the catheter implant entry site or the catheter tubing 27 or the end connector 25. Adaptation of the disclosed catheter protector harness apparatus to be incorporated with regular clothing may further enhance the desirability of the disclosed invention for use with hospitalized or ambulatory patients. Such use facilitates more normalized activity of the patient thereby making possible a happier, healthier, improved lifestyle resulting in an ultimately stronger patient unencumbered by the risks associated with implanted catheters and normal physical activity. Additionally, the exterior-most surface of the front middle portion 15, or flap 50, of the disclosed embodiment may be emblazoned with any number of desirable designs suitable to either patients or the trademarks and logos of health care facilities and other organizations desirous of promoting goodwill and their respective identities among catheter implant patients.

Figure 5:
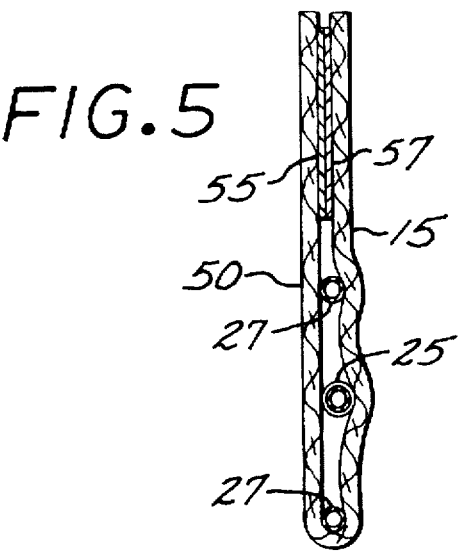
FIG. 5 is a cross-sectional view, in enlarged scale, taken along section line 5—5 of FIG. 3 with the catheter secured.

Reference to FIG. 5 reveals a cross-sectional view of the external segment of catheter tubing 27 and end connector 25 as they are stowed within the pocket or compartment formed by the above described embodiment. In the cross-sectional view of FIG. 6, the catheter tubing 27 is shown secured by fasteners 55 and 57 as catheter tubing passes across the boundary formed thereby, each fastener being located along the peripheral edge of the described pocket, wherein said tubing, 27 is protected and secured to the body. Fasteners 55 and 57 may be located along each peripheral edge of flap 50 and pocket portion 51 or simply along the periphery of the edge of flap 50 and pocket portion 51 opposite imaginary hinge-line 48.

As can be seen in FIG. 3, after the catheter tubing 27 and end connector 25 are stowed within the pocket formed by flap 50 and front middle section 15 of belt, the external portion of the catheter tubing 27 and the end connector 25, as well as the entry site of the catheter into the body, are completely protected and secured to the patient's body such that it can not be accidentally disturbed. From the preceding, it is readily apparent that the present invention facilitates protection and securement of the catheter without regard to where the entry site of the catheter into the body is located on the patient's torso. This flexibility in accommodating many different locations of catheter entry sites is highly desirable and a significant improvement over prior devices.

Referring to FIG. 4, it can be seen that configuring the catheter protector harness apparatus 10 with the ends 30 and 40 of belt 20 and with ends 70 of straps 65 bearing the fasteners 67 serves to both prevent unwanted rotation and to position such fasteners out of the patient's reach. Thus, while wearing the embodiment disclosed herein, the patient will be unable to rotate the belt 20 about the torso thereby ensuring that the belt 20 cannot be removed by the patient without assistance, unless otherwise desirable and belt 20 is configured with ends 30 and 40 positioned differently. Even more importantly, the external segment of the catheter will not be appreciably displaced from its nominal position while the harness is worn which ensures that disruption and irritation to the catheter entry site into the patient's body is minimized thereby eliminating a heretofore unsolved problem.

In application, harness 10 is first situated about the upper body of a patient with front middle section 15 of fabric belt 20 positioned proximal to the patient's chest. Opposite ends 30 and 40 are encircled around the torso so as to be positioned at the back (see FIGS. 2 and 4) whereafter end 40 is positioned on top of and pressed against end 30 thereby releasably engaging fastener 45 with cooperatively positioned fastener 35 thus securing fabric belt 20 about torso. Straps 65 are next wrapped over shoulders towards back side (FIG. 2 and 4) with ends 70 positioned on top of and pressed against ends 30 and 40 such that fasteners 67 of ends 70 are releasably engaged with fasteners 68 of ends 30 and 40 thus preventing the unwanted rotation of fabric belt 20 about torso. Catheter 27 and end 25 are then carefully tucked underneath, or placed outside front middle section 15, being thereby covered underneath pocket portion 51 or thereby covering said pocket portion 51, and resting against chest of patient. Flap 50 is then folded about imaginary hinge-line 48 underneath pocket portion 51, or over and outside pocket portion 51, such that catheter 27 and end 25 are enclosed by the pocket formed between flap 50 and pocket portion 51 such that fastener 55 is pressed against and releasably engaged against fastener 57 thus protectively securing catheter 27 and end 25 against the patient's chest.

In operation, thoracic catheter protector harness 10 protectively secures catheter 27 and end 25 from unwanted disruption. Further, as can be seen from FIGS. 3 and 4, the means for attaching the harness to the patient are located out of reach, if desired and configured as shown. During the normal movement experienced during rest or periods of activity, the harness straps 65 as situated about the shoulders serve to resist rotation of fabric belt 20 about the patient's torso, when said belt 20 is subjected to rotational forces, which ensures that the catheter implant site remains undisturbed and injury free. The convenience and effortlessness with which the harness is removed and reattached allows for quick and easy cleaning of both the harness itself and disinfection of the implanted catheter entry site into the skin.

While multiple forms of the invention have been illustrated and described, it is readily apparent that various modifications can be made without departing from the spirit and scope of the invention. For example, the straps 65 made be configured with fasteners on the ends proximal to front middle section 15 and opposite strap ends 70 so as to be completely detachable from fabric belt 20. Additionally, flap 50 may be configured with imaginary hinge-line 48 situated at the top, instead of the bottom as shown, of front middle section 15 so that flap 50 may be folded either down and underneath front middle section 15 instead of up and underneath as described above. Further, straps 65 may be of length sufficient to allow one strap to cross over the other as straps 65 pass across the patient's front or back instead of straight over the shoulder as shown in FIG. 3. As previously described, ends 30 and 40 of belt 20 may be reconfigured so as to permit removal by the wearer if such access is desirable. The preceding description of the preferred embodiment and the best mode for practicing the invention are provided for illustration purposes only and not for the purpose of limitation; the invention being defined by the claims.

What is claimed is:

1. Thoracic catheter protector harness apparatus for affixing an exposed segment of a catheter implanted in the body of a patient and comprising:

an elongated fabric belt for encircling said body and covering a catheter implant site, configured with a medial portion having on one side a pocket portion disposed to, when said harness is fastened about said body, face said body and further having first and second opposite ends;

first and second releasable attachment devices on the respective said first and second ends for releasably attaching together;

a flap mounted from said medial portion and having a continuous, unperforated wall and configured to fold upwardly and underneath said interior pocket portion of said medial portion to cooperate therewith in forming a compartment for receipt of said exposed segment, said compartment being disposed between said medial portion and said body;

said compartment being further formed with at least one tube securement fastener disposed about at least one peripheral edge of said flap, said tube fastener being adapted to slidably engage a portion of said exposed segment when said flap is folded over said medial portion, first and second releasable fasteners mounted on said medial portion and on said free end of said medial portion, respectively; and a stabilizing strap device projecting laterally from said belt to, when said apparatus is applied to said body pass in flanking relationship past a body extremity to, upon the application of rotary forces to said belt, engage said extremity and resist rotary movement of said belt about said body.

2. An thoracic catheter protector harness apparatus according to claim 1 wherein:

said stabilizing strap device includes at least one elongated shoulder strap fastened on one end to said belt near one of said opposite ends and on its opposite end to said medial portion and adapted to, when worn by said patient, pass over one of said patient's shoulders.

3. An thoracic catheter protector harness apparatus according to claim 1 wherein:

said stabilizing strap device includes a pair of elongated shoulder straps connected on the respective one end to said belt near the respective said opposite ends thereof and on their respective opposite ends to said medial portion.

4. An thoracic catheter protector harness apparatus according to claim 1 wherein:

said first and second releasable attachment devices including respective portions of hook and pile material adapted to releasably hook together.

5. An thoracic catheter protector harness apparatus according to claim 1 wherein:

said flap is configured to, when folded over on said medial portion, form said compartment to be elongated and open ended for receipt of said catheter.

6. An thoracic catheter protector harness apparatus according to claim 2 wherein:

said elongated fabric belt and said elongated shoulder strap are comprised of an elastic material.

7. An thoracic catheter protector harness apparatus according to claim 2 wherein:

said elongated fabric belt and said elongated shoulder strap are comprised of an inelastic material.

8. An thoracic catheter protector harness apparatus according to claim 2 wherein:

said elongated shoulder strap further comprises a proximal end and an distal end, said proximal and distal ends including hook and pile material adapted to releasably fasten said proximal end to said medial portion of said elongated fabric belt and to releasably and adjustably fasten said distal end to said opposite end of said elongated fabric belt.

9. An thoracic catheter protector harness apparatus according to claim 8 wherein:

said elongated fabric belt and said elongated shoulder strap are comprised of an elastic material.

10. An thoracic catheter protector harness apparatus according to claim 3 wherein:

said elongated fabric belt and said pair of elongated shoulder straps are comprised of an elastic material.

11. An thoracic catheter protector harness apparatus according to claim 3 wherein:

said pair of elongated shoulder straps each further comprise a proximal end and an distal end, said proximal and distal ends including hook and pile material adapted to releasably fasten said proximal ends to said medial portion of said elongated fabric belt and said distal ends to said opposite ends of said elongated fabric belt.

12. An thoracic catheter protector harness apparatus according to claim 5 wherein:

said flap further comprises an attachment end including hook and pile material adapted to releasably fasten said attachment end to said medial portion of said fabric belt.

13. An thoracic catheter protector harness apparatus according to claim 5 wherein:

said flap further comprises an attachment end including a medical grade adhesive adapted for repeated cleaning without degradation of adhesive capability and to releasably fasten said attachment end to said medial portion of said fabric belt.

14. An thoracic catheter protector harness apparatus according to claim 5 wherein:

said flap and said medial portion are of a construction including, within said compartment, a material resistant to staining from contact with blood, medical or other bodily substance and suitable for repeated cleaning.

15. An thoracic catheter protector harness apparatus according to claim 3 wherein:

said pair of elongated shoulder straps each further include a proximal end and a distal end wherein said proximal end is constructed to be integrally formed upon and depend from said medial portion of said belt.

* * * * *